(12) United States Patent
Takahashi et al.

(10) Patent No.: US 9,101,514 B2
(45) Date of Patent: Aug. 11, 2015

(54) METHOD OF EJECTING FAULTY ABSORBENT ARTICLE

(75) Inventors: Kazuhiko Takahashi, Fukushima (JP); Tomohiro Watanabe, Kagawa (JP); Masanobu Miyaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/130,155

(22) PCT Filed: Jun. 29, 2012

(86) PCT No.: PCT/JP2012/004260
§ 371 (c)(1),
(2), (4) Date: Mar. 24, 2014

(87) PCT Pub. No.: WO2013/005408
PCT Pub. Date: Jan. 10, 2013

(65) Prior Publication Data
US 2014/0197079 A1    Jul. 17, 2014

(30) Foreign Application Priority Data
Jul. 1, 2011    (JP) .................. 2011-147782

(51) Int. Cl.
*B07C 5/342* (2006.01)
*A61F 13/15* (2006.01)
(52) U.S. Cl.
CPC ..... *A61F 13/15764* (2013.01); *A61F 13/15772* (2013.01); *B07C 5/342* (2013.01)
(58) Field of Classification Search
CPC .... B07C 5/342; B07C 5/3422; G06T 7/0002; G06T 7/0004; A61F 13/15772
USPC ............ 209/552, 576, 939; 700/110; 382/141
See application file for complete search history.

(56) References Cited

U.S. PATENT DOCUMENTS 6,888,083 B2 *  5/2005  Hergeth ................ 209/576
8,583,279 B2 * 11/2013  Fecht ..................... 700/230
(Continued)

FOREIGN PATENT DOCUMENTS

EP    2 213 449 A1    8/2010
EP    2 554 278 A1    2/2013
(Continued)

OTHER PUBLICATIONS

International Search Report from corresponding PCT application No. PCT/JP2012/004260 dated Aug. 21, 2012 (1 pg).
(Continued)

*Primary Examiner* — Joseph C Rodriguez
(74) *Attorney, Agent, or Firm* — Brinks Gilson & Lione (57) ABSTRACT

A method of ejecting a faulty absorbent article which includes a step of detecting a failure region of an absorbent article in which a failure location of the absorbent article exists, and a type of a failure in the failure region, by identifying a shape of the absorbent article in the course of the manufacturing line, a step of deciding the absorbent article to be ejected based on the detection result of the failure region and the type of failure in the step of detecting, and a step of disengaging, from the manufacturing line, the absorbent article decided in the step of deciding, and then ejecting the absorbent article in the course of the manufacturing line. In the step of deciding, the number of absorbent articles to be ejected in the step of ejecting is decided according to the failure region and the type of the failure.

4 Claims, 6 Drawing Sheets

(56) References Cited

U.S. PATENT DOCUMENTS

| | | | |
|---|---|---|---|
| 8,712,570 B2* | 4/2014 | Kent et al. | 700/110 |
| 2001/0038709 A1* | 11/2001 | Bett et al. | 382/141 |
| 2003/0110739 A1* | 6/2003 | Saas | 53/460 |
| 2010/0305739 A1 | 12/2010 | DeBruler et al. | |
| 2013/0001042 A1* | 1/2013 | Yamamoto | 198/367.1 |
| 2013/0062263 A1* | 3/2013 | Nakano | 209/552 |
| 2014/0339046 A1* | 11/2014 | Wiedmann et al. | 198/341.01 |

FOREIGN PATENT DOCUMENTS

| | | |
|---|---|---|
| GB | 687865 | 2/1953 |
| JP | 10-263010 | 10/1998 |
| JP | 2002-079187 | 3/2002 |
| JP | 2010-200908 | 9/2010 |
| WO | WO 2011/118493 A1 | 9/2011 |

OTHER PUBLICATIONS

European extended Search Report from corresponding European application No. 12808129.6 dated Jan. 5, 2015 (6 pgs).

Egyptian Office Action from corresponding Egyptian application No. Mar. 2014 dated Mar. 16, 2015 (6 pgs).

* cited by examiner

METHOD OF EJECTING FAULTY ABSORBENT ARTICLE

RELATED APPLICATION

This application is a 35 U.S.C. §371 national phase filing of International Patent Application No. PCT/JP2012/004260, filed Jun. 29, 2012, through which and to which priority is claimed under 35 U.S.C. §119 to Japanese Patent Application No. 2011-147782, filed Jul. 1, 2011.

TECHNICAL FIELD

The present invention relates to a method of ejecting a faulty absorbent article used in a manufacturing line of an absorbent article.

BACKGROUND ART

Conventionally, an absorbent article such as a disposable diaper or a sanitary napkin is generally manufactured by using a manufacturing line in which an absorber, for example, is arranged sequentially on a continuous web conveyed by a belt conveyor, for example, and the manufacturing line includes a step of folding and a step of cutting the continuous web.

In such a manufacturing line, generally, an ejection mechanism is provided, by which an absorbent article for which a processing failure is determined is disengaged from the manufacturing line, and the absorbent article is ejected in the course of the manufacturing line. Because the manufacturing line operates at a high speed, normally, a plurality of preceding and succeeding absorbent articles including the absorbent article for which a processing failure is determined are ejected in succession.

Therefore, an ejection method by which the plurality of absorbent articles are ejected after printing a number and a symbol on the absorbent article is known (for example, see PTL 1). Specifically, continuous numbers, or symbols such as a circle and a triangle are printed on the plurality of absorbent articles, and the plurality of absorbent articles on which the numbers or the symbols are printed are ejected.

According to such an ejection method, the operator can easily adjust the timing of ejection of the absorbent article such that among the plurality of absorbent articles that are ejected, the position of the absorbent article for which a processing failure is determined is generally at the center (for example, the third absorbent article when five absorbent articles are ejected).

CITATION LIST

Patent Literature

PTL 1: Japanese Patent Unexamined Publication No. 2002-791187 (Page No. 3, FIG. 1)

SUMMARY OF INVENTION

Technical Problem

However, the aforementioned conventional method of ejecting an absorbent article has the below-mentioned problem. That is, a certain number of absorbent articles for which a processing failure is not determined are also ejected together with the absorbent article for which a processing failure is determined, and because the ejected absorbent articles cannot be handled as products, an obstruction in improvement of the yield rate is a problem.

Therefore, the present invention has been developed in view of such a situation, and an object thereof is to provide a method of ejecting an absorbent article, by which at the time of ejecting an absorbent article for which a processing failure is determined, the simultaneous ejection of absorbent articles for which a processing failure is not determined can be prevented.

Solution to Problem

The present invention provides a method of ejecting a faulty absorbent article used in a manufacturing line of an absorbent article having a plurality of steps for a conveyed continuous web, which method comprises: a step of detecting a failure region of an absorbent article in which a failure location of the absorbent article exists, and a type of a failure in the failure region, by identifying a shape of the absorbent article in the course of the manufacturing line; a step of deciding to eject a faulty absorbent article based on the detection result of the failure region and the type of failure in the step of detecting; and a step of disengaging, from the manufacturing line, the absorbent article decided in the step of deciding, and then ejecting the absorbent article in the course of the manufacturing line, wherein in the step of deciding, the number of absorbent articles to be ejected in the step of ejecting is decided according to the failure region and the type of the failure.

Advantageous Effect of Invention

According to one characteristic of the present invention, it is possible to provide a method of ejecting an absorbent article, by which at the time of ejecting an absorbent article for which a processing failure is determined, the simultaneous ejection of absorbent articles for which a processing failure is not determined can be prevented.

DESCRIPTION OF EMBODIMENTS

Next, an embodiment of a method of ejecting an absorbent article according to the present invention is explained with reference to drawings. In the following description of the drawings, the same or similar reference numerals are used to designate the same or similar parts. It will be appreciated that the drawings are schematically shown and the ratio and the like of each dimension may be different from the real ones.

Accordingly, specific dimensions should be determined in consideration of the explanation below. Moreover, among the drawings, the respective dimensional relations or ratios may differ.

(1) Entire Schematic Configuration of Manufacturing Line

Figure 1:
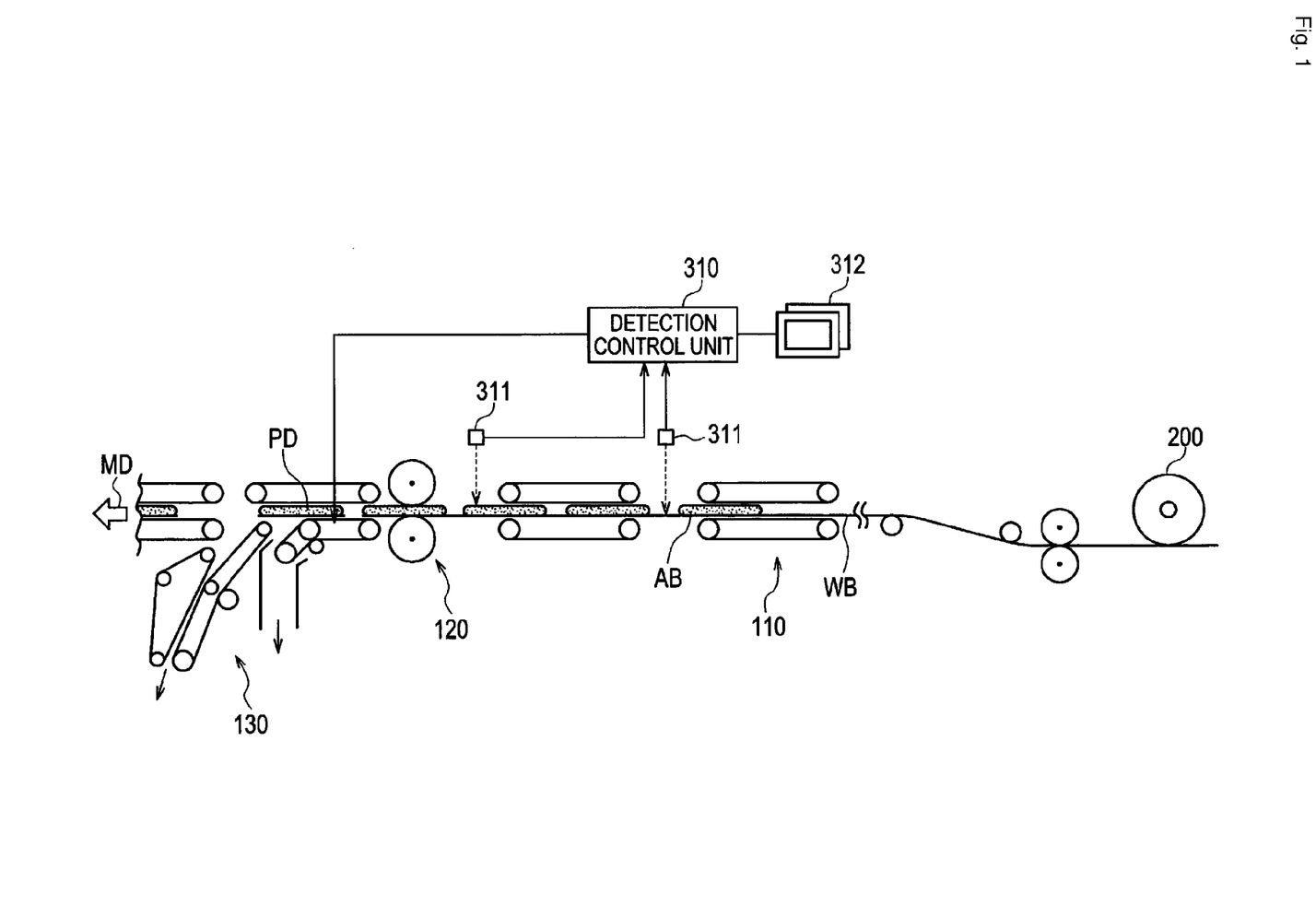
FIG. 1 is a schematic diagram showing an entire configuration of a manufacturing line 10 of an absorbent article according to an embodiment of the present invention.

FIG. 1 is a schematic diagram showing an entire configuration of a manufacturing line 10 of an absorbent article according to the present embodiment. The manufacturing line 10 is configured by a plurality of devices configured to manufacture an absorbent article, specifically, an absorbent article PD having an absorber AB for absorbing liquids, such as a disposable diaper, a sanitary napkin, or a panty liner, etc. The absorber AB is configured from pulp and an absorbent polymer. The explanation of the present embodiment is based on a manufacturing line 10 configured to manufacture a disposable diaper. Furthermore, the manufacturing line 10 shown in FIG. 1, is a simplified illustration of the manufacturing steps of the absorbent article PD, and depending on the type of the absorbent article PD, various other steps are included in the manufacturing line 10.

The manufacturing line 10 conveys a continuous web WB, which is a continuous body of a nonwoven fabric and a resin film, towards a machine direction MD, and arranges the absorber AB on the conveyed continuous web WB, and finally manufactures the absorbent article PD by folding and cutting the continuous web WB while conveying the continuous web WB.

Specifically, the manufacturing line 10 includes a conveyor 110, a product cutter 120, and an ejection device 130.

The conveyor 110 is configured to convey the continuous web WB at a high speed along the machine direction MD, and is configured by a plurality of belt conveyors. Depending on the conveyance position, and the type of the continuous web WB to be conveyed and the absorbent article PD, a suction-type belt conveyor in which a plurality of through-holes are formed, and that has a suction function is used, if necessary.

The product cutter 120 cuts the continuous web WB on which the absorbent articles PD are arranged at predetermined intervals (that is, the product length of the absorbent article PD). The product cutter 120 is provided with a blade for cutting, and configured by a cutter roller rotating in the machine direction MD and an anvil roller facing the cutter roller and rotating similarly in the machine direction MD.

The ejection device 130 is configured to disengage the absorbent article PD having a manufacturing-related failure location, that is, a processing failure, from the manufacturing line 10, and to eject the absorbent article PD in the course of the manufacturing line 10. Specifically, the ejection device 130 is configured by a guide bar (not shown in the figure) configured to guide the conveyed absorbent article PD to an ejection route, and a suction-type belt conveyor arranged towards the ejection route side, for example. Particularly, in the present embodiment, in order to improve the yield rate of the absorbent article PD, the ejection device 130 is configured to eject either only the absorbent article PD having a failure location, or the absorbent article PD having a failure location, as well as the adjoining absorbent articles PD that exist before and after the absorbent article PD.

Furthermore, in order to detect the shape and state of the conveyed continuous web WB and the manufactured absorbent article PD, the manufacturing line 10 includes a detection control unit 310, cameras 311, and an image monitor 312.

The detection control unit 310 is connected to the plurality of cameras 311 installed at a predetermined position on the manufacturing line 10 (for example, immediately after each step).

Based on the images shot by the camera 311 showing the shape and state of the continuous web WB or the absorbent article PD, the detection control unit 310 identifies the absorbent article PD in which a failure location exists. Specifically, by identifying the shape of the absorbent article PD in the course of the manufacturing line 10, the detection control unit 310 detects a failure region of the absorbent article PD in which a failure location exists, for example, the central portion CT in the machine direction MD (conveyance direction) of the absorbent article PD, as well as the type of failure in the failure region, for example, a lamination failure of the absorber AB.

Based on the detection results of the failure region and the type of failure, the detection control unit 310 decides the absorbent articles PD that must be ejected, and instructs the timing of ejection of the absorbent articles PD that are decided to be ejected, as well as the number of absorbent articles PD to be ejected, to the ejection device 130.

Figure 2:
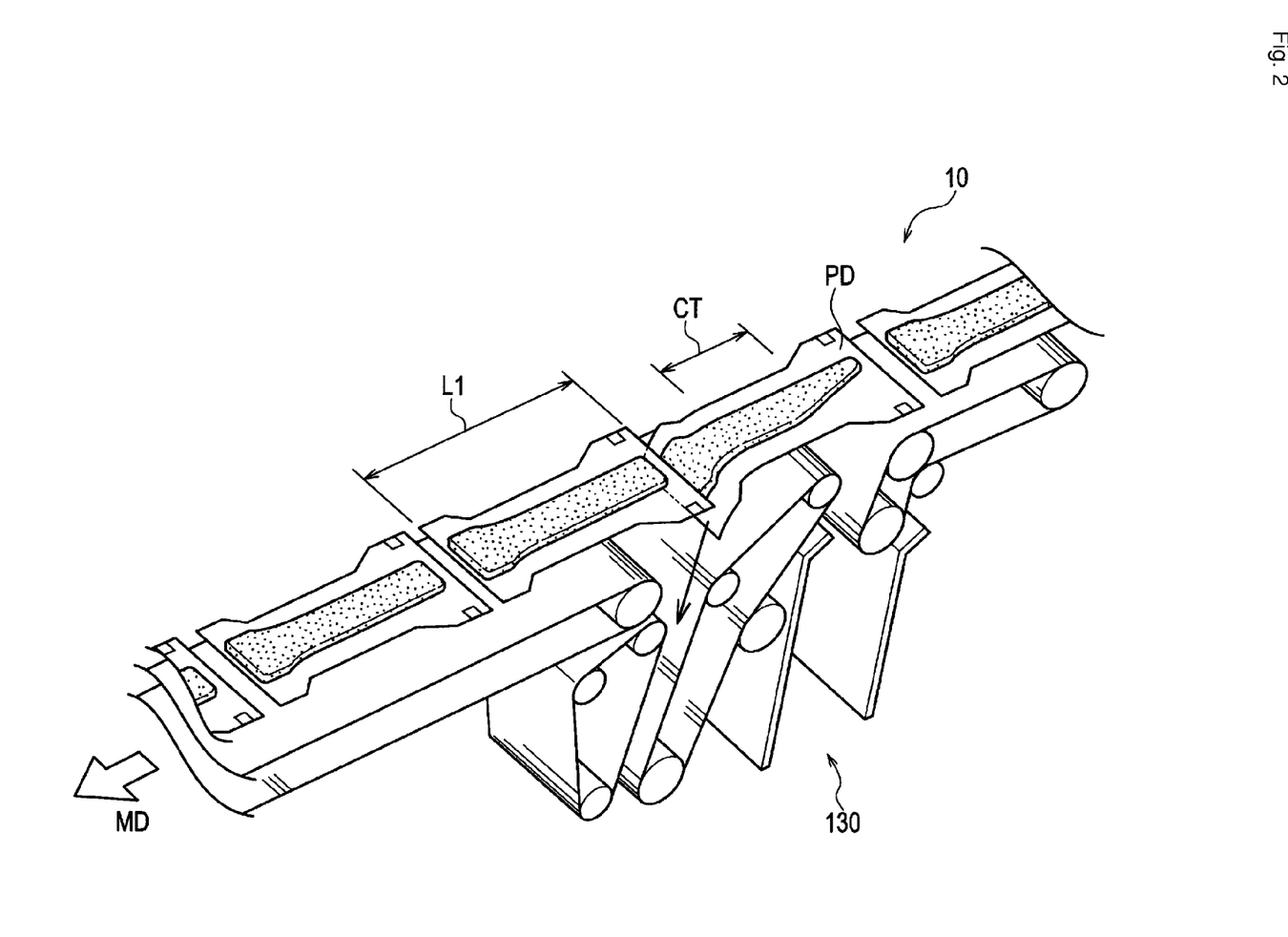
FIG. 2 is a partially expanded perspective view of an ejection device 130 according to the embodiment of the present invention.

FIG. 2 is a partially expanded perspective view of the ejection device 130. As shown in FIG. 2, the ejection device 130 disengages the absorbent article PD having a failure region from the manufacturing line 10, and ejects the absorbent article PD in the course of the manufacturing line 10.

Specifically, as in the example shown in FIG. 2, based on the instruction from the detection control unit 310, the ejection device 130 leads the absorbent article PD in which a lamination failure (failure location) of the absorber AB exists in the central portion CT, to the ejection route (see the arrow in the figure) by using a guide bar and a suction-type belt conveyor. For example, the guide bar is deployed above the absorbent article PD and moves below when the absorbent article PD to be ejected passes through the guide bar. Further, the suction-type belt conveyor is deployed along the ejecting direction (see arrow in FIG. 2). The suction type belt conveyor guides the absorbent article PD to be ejected to the ejection route by suctioning the absorbent article PD. The absorbent articles PD in which a failure location does not exist are not ejected by the ejection device 130, but are conveyed to the next step.

(2) Ejection Operation of the Absorbent Article

Figure 3:
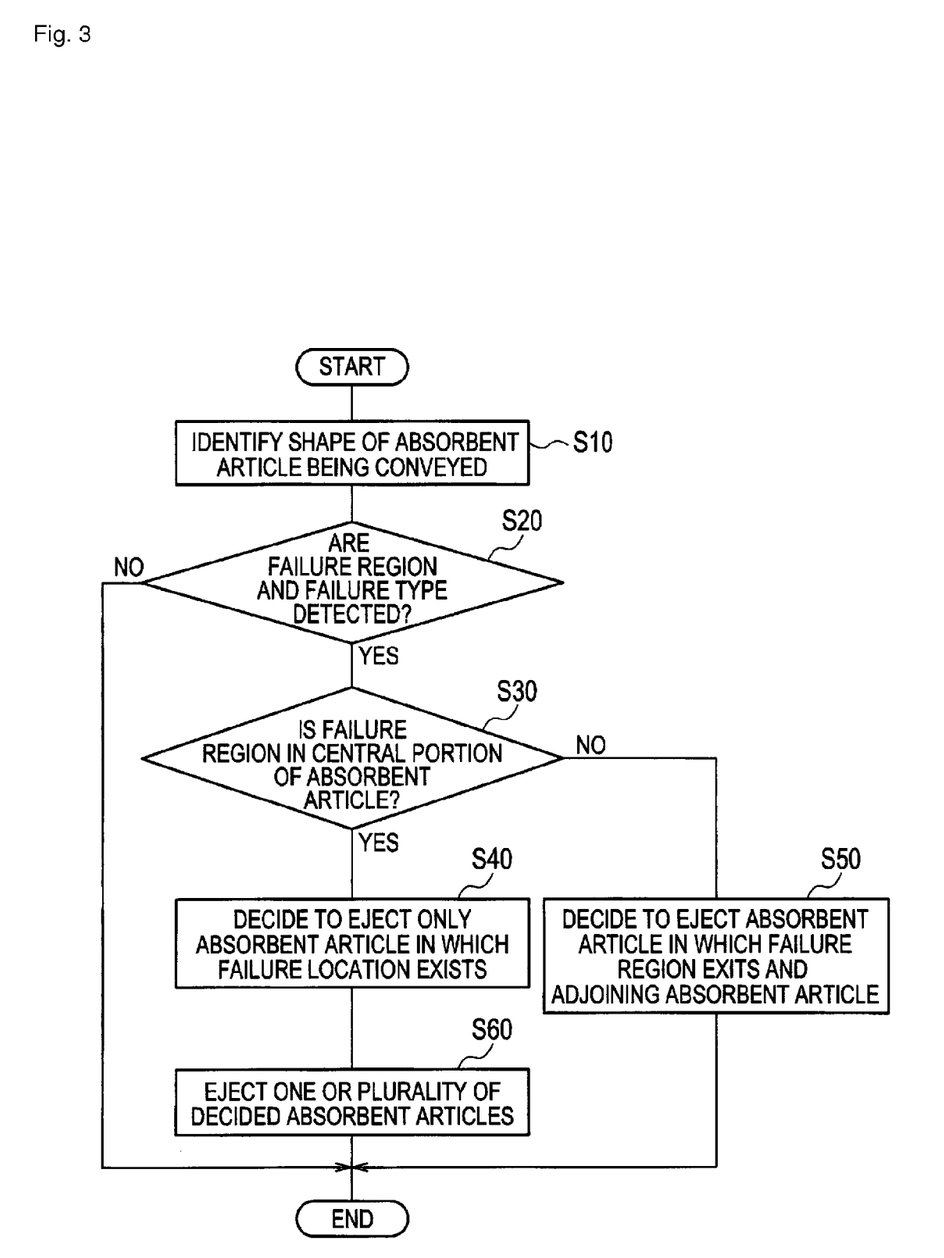
FIG. 3 is a diagram illustrating an ejection operation flow of an absorbent article PD in the manufacturing line 10 according to the embodiment of the present invention.

FIG. 3 illustrates the ejection operation flow of the absorbent article PD in the manufacturing line 10. Specifically, FIG. 3 illustrates the operation flow of the manufacturing line 10 concerning the ejection of an absorbent article PD that may include a failure region.

As shown in FIG. 3, the detection control unit 310 of the manufacturing line 10 acquires images showing the shape of the continuous web WB being conveyed as well as that of the absorbent article PD by using the cameras 311, and identifies the shape of the absorbent article PD (or of the semi-finished absorbent article PD) based on the acquired images (S10). That is, the detection control unit 310 identifies the shape of the absorbent article PD in the course of the manufacturing line 10.

Next, by comparing the images shot by the cameras 311 showing the shape of the continuous web WB and the absorbent article PD, and the already-stored predetermined shape, the detection control unit 310 performs a process to determine whether or not the continuous web WB or the absorbent article PD includes a failure region. As a result of such a process, the detection control unit 310 determines whether or not a failure region is detected in the absorbent article PD (S20). The detection control unit 310 simultaneously detects the failure region and the type of failure.

As described above, in the present embodiment, the failure region is divided into the central portion CT in the machine direction MD (conveyance direction) of the absorbent article PD, and the region other than the central portion CT (that is, both ends in the machine direction MD of the absorbent article PD). The failure region may be divided further.

Furthermore, in the present embodiment, (i) transfer failure of waist gathers, (ii) lamination failure of the absorber AB on the continuous web WB, and (iii) gluing failure of the sidesheets, the topsheet, the absorber AB, and the backsheet are explained as examples of the types of failures.

The detection control unit 310 determines whether or not the detected failure region is the central portion CT of the absorbent article PD (S30). The central portion CT is the region including 30% or less of the dimension L1 (see FIG. 2) of the absorbent article PD from the center of the absorbent article PD in the machine direction MD (conveyance direction). That is, the central portion CT is the region including 60% of the dimension L1 with the center of the absorbent article PD in the machine direction MD as the reference.

Based on the detection results of the failure region and the type of failure, the detection control unit 310 decides the absorbent article PD that must be ejected, that is, the absorbent article PD having a failure region, or possibly having a failure region (S40, S50).

Specifically, the detection control unit 310 decides the number of absorbent articles PD to be ejected depending on the failure region and the type of failure. When the failure region is positioned in the central portion CT, the detection control unit 310 decides that only the absorbent article PD having the failure region is to be ejected (S40).

On the other hand, when the failure region is positioned in other than the central portion CT, the detection control unit 310 decides that the absorbent article PD in which the failure location exists, and the absorbent articles PD adjoining in the failure region side (front or back absorbent articles in the conveyance direction) are to be ejected (S50).

Figure 4:
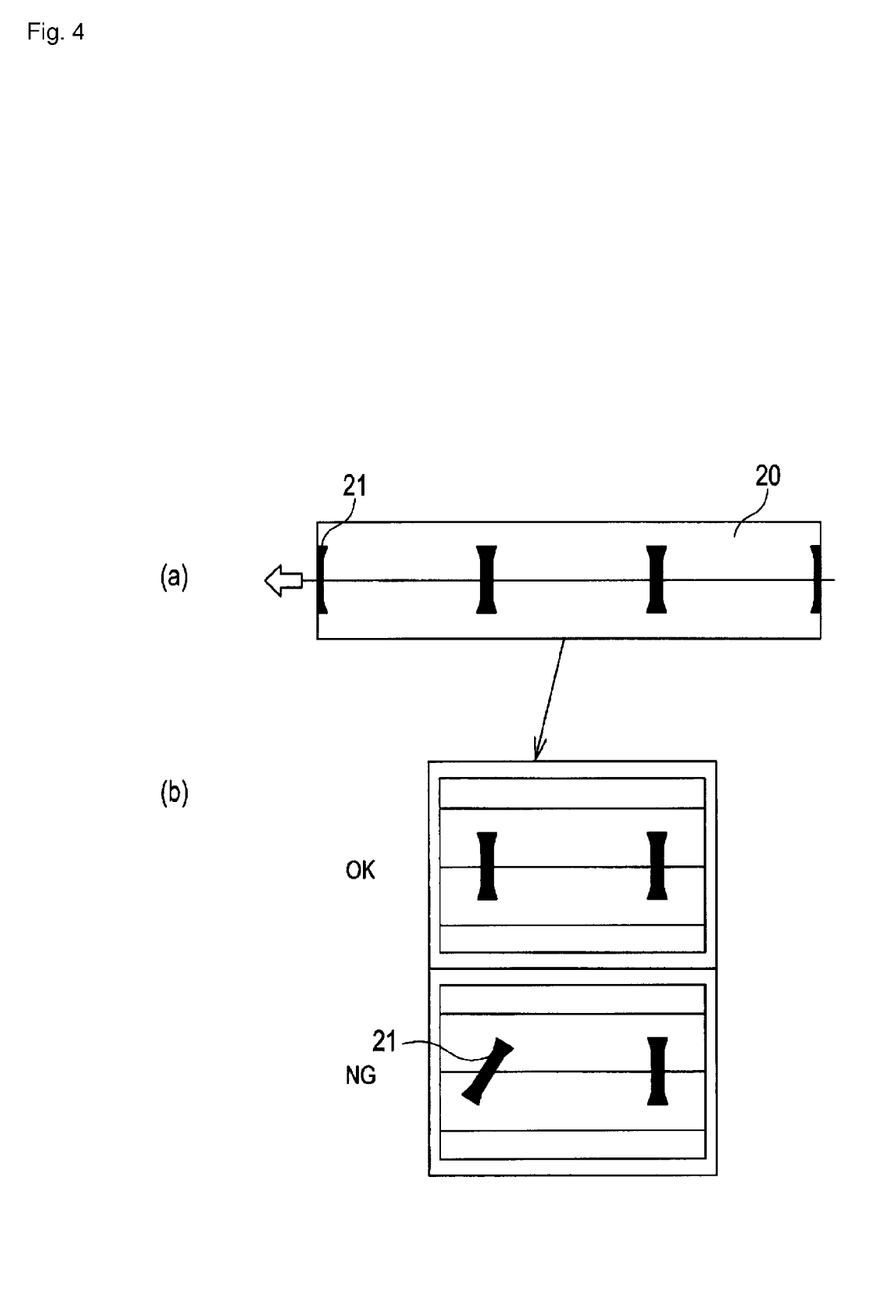
FIG. 4 is a diagram illustrating an example of occurrence of a transfer failure of waist gathers according to an embodiment of the present invention.
Figure 5:
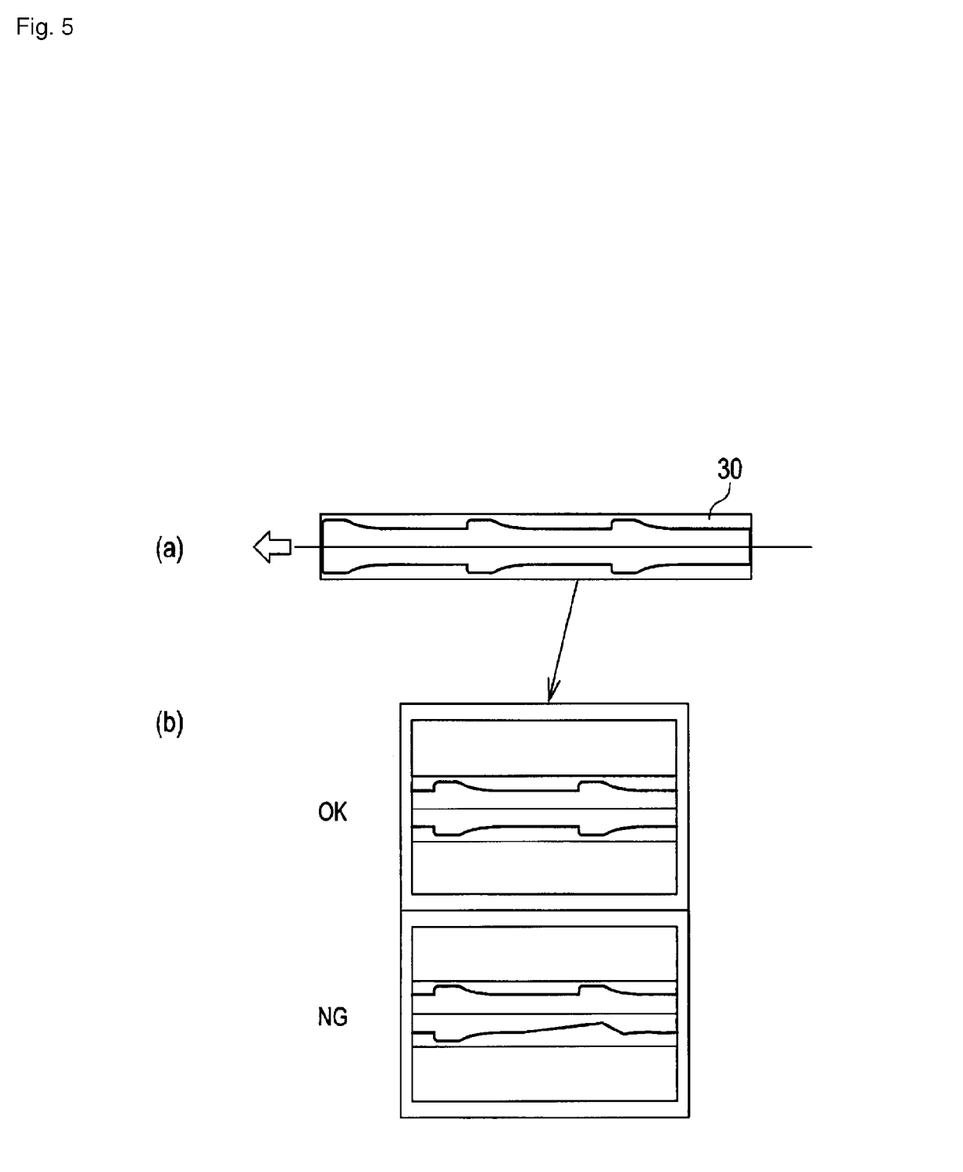
FIG. 5 is a diagram illustrating an example of occurrence of a lamination failure of an absorber AB on a continuous web WB according to an embodiment of the present invention.
Figure 6:
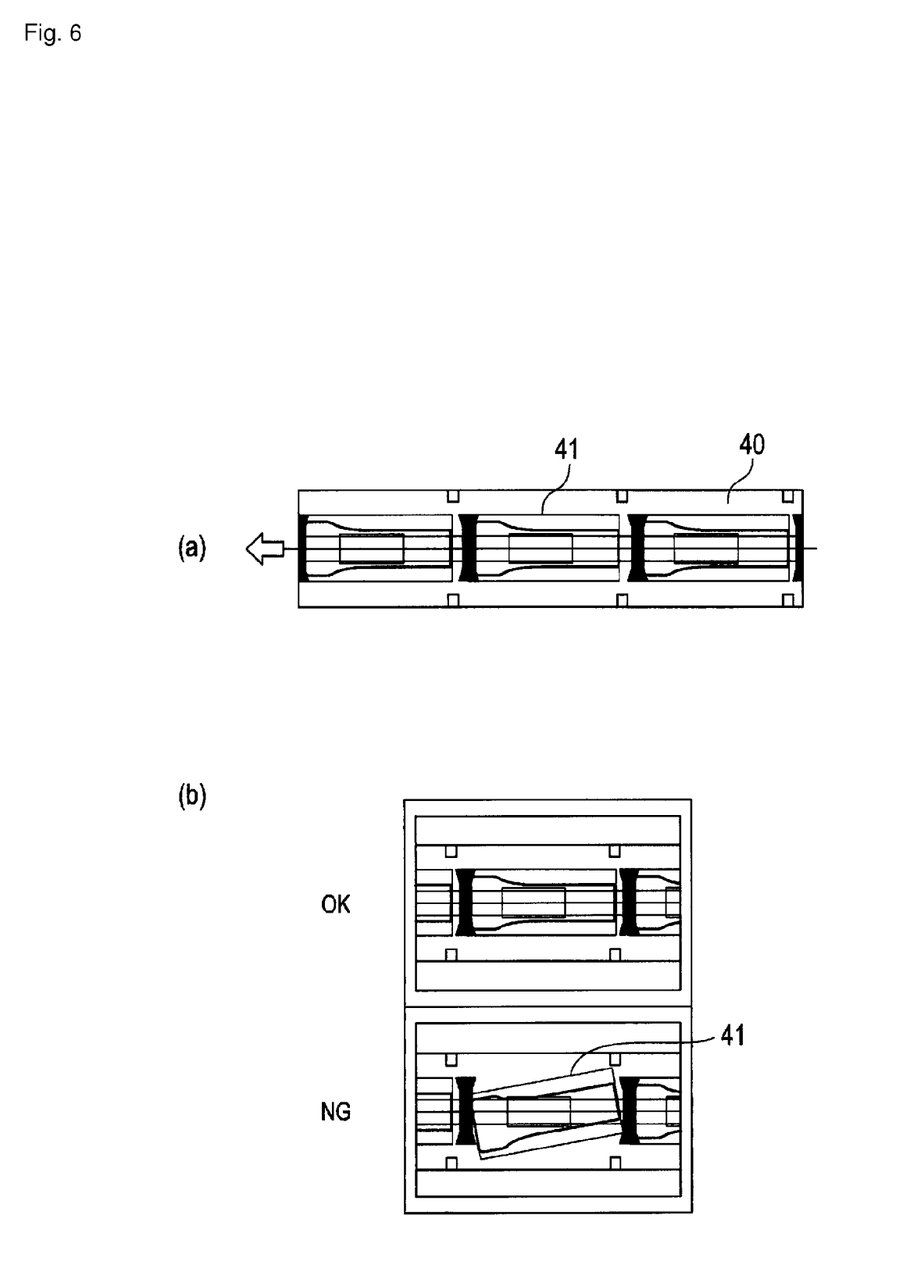
FIG. 6 is a diagram illustrating an example of occurrence of a pasting failure of a sidesheet, a topsheet, the absorber AB, and a backsheet according to an embodiment of the present invention.

Here, FIGS. 4(*a*), (*b*), FIGS. 5(*a*), (*b*), and FIGS. 6(*a*), (*b*) illustrate examples of occurrence of the types of failure.

FIGS. 4(*a*), (*b*) illustrate an example of occurrence of a transfer failure of waist gathers. FIG. 4(*a*) shows the backsheet 20 and waist gathers 21 (elastic members) provided in the backsheet 20. FIG. 4 (*b*) shows the shape (image) of the waist gathers 21 when a transfer failure does not occur (OK), as well as the shape (image) of the waist gathers 21 when a transfer failure occurs (NG). That is, FIG. 4(*b*) shows the state when the images shot by the camera 311 are displayed on the image monitor 312 (FIG. 5(*b*) and FIG. 6(*b*) are also the same). In the NG example, because the waist gathers 21 are arranged at an inclination with respect to the backsheet 20, it is determined that a transfer failure has occurred.

FIGS. 5(*a*), (*b*) illustrate an example of occurrence of a lamination failure of the absorber AB on the continuous web WB. FIG. 5(*a*) shows an absorber line 30 in which the absorbers AB prior to being cut are arranged in continuation. FIG. 5(*b*) shows the shape (image) of the absorber line 30 when a lamination failure does not occur (OK), as well as the shape (image) of the absorber line 30 when a lamination failure occurs (NG). In the NG example, because lamination is performed when the ends of the absorber line 30 are folded, it is determined that a lamination failure has occurred.

FIGS. 6(*a*), (*b*) illustrate an example of occurrence of a gluing failure of the sidesheets, the topsheet, the absorber AB, and the backsheet. FIG. 6(*a*) shows a laminated body line 40 in which the sidesheets, the topsheet, the absorber AB, and the backsheet are pasted together, and a laminated body 41 of the absorber AB and the sidesheets. FIG. 6(*b*) shows the shape (image) of the laminated body line 40 when a pasting failure does not occur (OK), as well as the shape (image) of the laminated body line 40 when a pasting failure occurs (NG). That is, in the NG example, because the laminated body 41 is arranged at an inclination with respect to the laminated body line 40, it is determined that a pasting failure has occurred.

Here, when the type of failure is an absorber AB or cushion sheet failure, the detection control unit 310 can decide that only the absorbent article PD having the failure region is to be ejected. On the other hand, in the case of a transfer failure of a waist gather, because there is a high possibility that the absorbent articles PD immediately before and immediately after the absorbent article PD having the failure region will be affected by the processing failure, the detection control unit 310 can decide that two absorbent articles PD, that is, the absorbent article PD having the failure region, as well as an absorbent article PD; an absorbent article PD immediately before or immediately after the absorbent article PD having the failure region, are to be ejected.

Furthermore, in the above-mentioned step of deciding the absorbent article PD that must be ejected, when the type of the failure is related to members spanning a plurality of absorbent articles PD, the detection control unit 310 may decide that the plurality of absorbent articles PD including the absorbent article PD having the failure region are to be ejected. A case in which the type of the failure is related to members spanning a plurality of absorbent articles PD is related to the elastic members (for example, waist gathers and solid gathers) provided continuously in the machine direction MD.

Additionally, also in the case when the type of the failure is the addition of foreign substances, the detection control unit 310 may decide that a plurality of absorbent articles PD including the absorbent article PD having the failure region are to be ejected. Examples of foreign substances include drippings of the hot melt adhesive handled in the manufacturing line 10, and broken pieces of other members.

In order to eject one or the plurality of absorbent articles PD decided as described above, the detection control unit 310 instructs the timing of ejection of the absorbent articles PD that are decided to be ejected, as well as the ejection time to the ejection device 130, and the ejection device 130 ejects the absorbent article PD (S60).

(3) Operation and Effect

According to the manufacturing line 10 of the present embodiment, the number of the absorbent articles PD to be ejected is decided depending on the failure region and the type of failure. Specifically, when the failure region is positioned in the central portion CT of the absorbent article PD, it is decided that only the absorbent article PD in which the failure location exists is to be ejected. On the other hand, when the failure region is positioned in other than the central portion CT, it is decided that the absorbent article PD in which the failure location exists, and the absorbent articles PD adjoining in the failure region side are to be ejected.

Therefore, the absorbent articles PD that may possibly have a failure region are limited, and only the limited absorbent articles PD can be ejected. That is, as in the conventional method of ejecting an absorbent article, the ejection of a certain number of absorbent articles for which a processing failure is not determined, together with the absorbent article for which a processing failure is determined is prevented.

That is, according to the manufacturing line 10, at the time of ejecting an absorbent article for which a processing failure is determined, the simultaneous ejection of absorbent articles for which a processing failure is not determined, as seen conventionally, can be prevented.

In the present embodiment, when the type of the failure is related to members spanning a plurality of absorbent articles PD, it can be decided that the plurality of absorbent articles PD including the absorbent article PD having the failure region are to be ejected. Additionally, even in the case when the type of the failure is the addition of foreign substances, it can be decided that a plurality of absorbent articles PD including the absorbent article PD having the failure region are to be ejected. Therefore, only the absorbent article PD in which a failure location possibly exists can be ejected more certainly.

(4) Other Embodiments

So far, the present invention is disclosed through the above embodiment. However, it should not be interpreted that the statements and drawings constituting a part of the present disclosure limit the present invention. From this disclosure, a variety of alternate embodiments, examples, and applicable techniques will become apparent to one skilled in the art.

For example, in the aforementioned embodiment, in cases where the type of the failure is related to members spanning a plurality of absorbent articles PD, and where the type of the failure is the addition of foreign substances, the plurality of absorbent articles PD including the absorbent article PD having a failure region can be ejected, however, such an operation need not necessarily be performed. That is, even in cases where the type of the failure is related to members spanning a plurality of absorbent articles PD, and where the type of the failure is the addition of foreign substances, only the absorbent article PD having the failure region may be ejected.

Furthermore, in the aforementioned embodiment, the detection control unit 310 simultaneously detected the failure region and the type of failure; however, the detection of the failure region and the type of failure need not necessarily be performed simultaneously.

In the aforementioned embodiment, an open-type disposable diaper was explained as an example; however, the present invention can be certainly applied to a sanitary napkin or a panty liner.

As described above, needless to say, the present invention includes various embodiments and the like not described here. Therefore, the technical range of the present invention is to be defined only by the inventive specific matter according to the adequate claims from the above description.

REFERENCE SIGNS LIST

10 Manufacturing line
20 Backsheet
21 Waist gathers
30 Absorber line
40 Laminated body line
41 Laminated body
110 Conveyor
120 Product cutter
130 Ejection device
310 Detection control unit
311 Camera
312 Image monitor
AB Absorber
PD Absorbent article
WB Continuous web

The invention claimed is:

1. A method of ejecting a faulty absorbent article used in a manufacturing line of an absorbent article having a plurality of steps for a conveyed continuous web, comprising:
   a step of detecting a failure region of an absorbent article in which a failure location of the absorbent article exists, and a type of a failure in the failure region, by identifying a shape of the absorbent article in the course of the manufacturing line;
   a step of deciding to eject a faulty absorbent article based on the detection result of the failure region and the type of failure in the step of detecting; and
   a step of disengaging, from the manufacturing line, the absorbent article decided in the step of deciding, and then ejecting the absorbent article in the course of the manufacturing line, wherein
   in the step of deciding, the number of absorbent articles to be ejected in the step of ejecting is decided according to the failure region and the type of the failure.

2. The method of ejecting a faulty absorbent article according to claim 1, wherein in the step of deciding, when the failure region is positioned in the central portion of the absorbent article in a conveyance direction of the continuous web, it is decided that only the absorbent article in which the failure location exists is to be ejected, and when the failure region is positioned in other than the central portion of the absorbent article in a conveyance direction of the continuous web, it is decided that the absorbent article in which the failure location exists, and the absorbent articles adjoining in the failure region side are to be ejected.

3. The method of ejecting a faulty absorbent article according to claim 1, wherein in the step of deciding, when the type of the failure is related to members spanning the plurality of absorbent articles, it is decided in the step of ejecting that the plurality of absorbent articles including the absorbent article having the failure region are to be ejected.

4. The method of ejecting a faulty absorbent article according to claim 1, wherein in the step of deciding, when the type of the failure is the addition of foreign substances, it is decided in the step of ejecting that a plurality of absorbent articles including the absorbent article having the failure region are to be ejected.

* * * * *